(12) United States Patent
Tran

(10) Patent No.: US 12,629,029 B2
(45) Date of Patent: May 19, 2026

(54) ELECTRO-ANATOMICAL MAPPING WITHOUT ACQUIRING A REFERENCE SIGNAL

(71) Applicant: Biosense Webster (Israel) Ltd., Yokneam (IL)

(72) Inventor: Brandon Andrew Tran, Madison, WI (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 690 days.

(21) Appl. No.: 17/742,965

(22) Filed: May 12, 2022

(65) Prior Publication Data

US 2023/0363643 A1 Nov. 16, 2023

(51) Int. Cl.
*A61B 5/00* (2006.01)
*A61B 5/282* (2021.01)
*A61B 5/283* (2021.01)
*A61B 5/341* (2021.01)

(52) U.S. Cl.
CPC ............ *A61B 5/0044* (2013.01); *A61B 5/282* (2021.01); *A61B 5/283* (2021.01); *A61B 5/341* (2021.01)

(58) Field of Classification Search
CPC .............. A61B 5/00; A61B 5/28; A61B 5/367
See application file for complete search history.

(56) References Cited

U.S. PATENT DOCUMENTS

| | | | |
|---|---|---|---|
| 6,892,091 B1 | 5/2005 | Ben-Haim et al. | |
| 8,137,343 B2 | 3/2012 | Harlev et al. | |
| 8,401,625 B2 | 3/2013 | Harlev et al. | |
| 8,463,368 B2 | 6/2013 | Harlev et al. | |
| 8,615,287 B2 | 12/2013 | Harlev et al. | |
| 9,259,165 B2 | 2/2016 | Rubinstein et al. | |
| 9,398,862 B2 | 7/2016 | Harlev et al. | |
| 10,201,288 B2 | 2/2019 | Harlev et al. | |
| 10,285,611 B1 | 5/2019 | Harlev et al. | |
| 11,013,447 B2 | 5/2021 | Harlev et al. | |
| 2008/0249424 A1 | 10/2008 | Harlev et al. | |
| 2009/0177071 A1 | 7/2009 | Harlev et al. | |

(Continued)

FOREIGN PATENT DOCUMENTS

| | | | | |
|---|---|---|---|---|
| GB | 2573109 A | 10/2019 | | |
| WO | WO-2021084255 A1 * | 5/2021 | ............. | A61B 5/053 |

OTHER PUBLICATIONS

International Search Report and Written Opinion mailed on Aug. 31, 2023 for PCT Patent Application No. PCT/IB2023/054592.

*Primary Examiner* — Lynsey C Eiseman
(74) *Attorney, Agent, or Firm* — Volpe Koenig

(57) ABSTRACT

Systems and methods are disclosed for generating an electro-anatomical map of the heart. Techniques disclosed include measuring groups of activation signals. The activation signals of each group are measured by respective electrodes of a mapping catheter that is placed at a respective position in the heart. Where at least one electrode of the mapping catheter that measured an activation signal of one group spatially overlapped with a respective electrode of the mapping catheter that measured an activation signal of another group. Techniques disclosed further include obtaining, based on the groups of activation signals, respective sets of time measurements, utilizing the overlapping electrodes. And, constructing the electro-anatomical map based on the obtained sets of time measurements.

20 Claims, 7 Drawing Sheets

(56)        References Cited

U.S. PATENT DOCUMENTS

| | | |
|---|---|---|
| 2009/0177072 A1 | 7/2009 | Harlev et al. |
| 2009/0253976 A1 | 10/2009 | Harlev et al. |
| 2009/0281439 A1 | 11/2009 | Harlev et al. |
| 2010/0106009 A1 | 4/2010 | Harlev et al. |
| 2010/0106154 A1 | 4/2010 | Harlev et al. |
| 2010/0274150 A1 | 10/2010 | Harlev et al. |
| 2010/0286550 A1 | 11/2010 | Harlev et al. |
| 2010/0286551 A1 | 11/2010 | Harlev et al. |
| 2010/0305433 A1 | 12/2010 | Harlev et al. |
| 2010/0324414 A1 | 12/2010 | Harlev et al. |
| 2011/0160574 A1 | 6/2011 | Harlev et al. |
| 2011/0190625 A1 | 8/2011 | Harlev et al. |
| 2011/0275949 A1 | 11/2011 | Harlev et al. |
| 2011/0282186 A1 | 11/2011 | Harlev et al. |
| 2011/0282187 A1 | 11/2011 | Harlev et al. |
| 2012/0078077 A1 | 3/2012 | Harlev et al. |
| 2012/0130267 A1 | 5/2012 | Harlev et al. |
| 2012/0143030 A1 | 6/2012 | Harlev et al. |
| 2012/0184858 A1 | 7/2012 | Harlev et al. |
| 2012/0184863 A1 | 7/2012 | Harlev et al. |
| 2012/0184864 A1 | 7/2012 | Harlev et al. |
| 2012/0184865 A1 | 7/2012 | Harlev et al. |
| 2012/0253161 A1 | 10/2012 | Harlev et al. |
| 2012/0277567 A1 | 11/2012 | Harlev et al. |
| 2013/0006084 A1 | 1/2013 | Harlev et al. |
| 2013/0109945 A1 | 5/2013 | Harlev et al. |
| 2013/0253298 A1 | 9/2013 | Harlev et al. |
| 2013/0261483 A1 | 10/2013 | Harlev et al. |
| 2013/0345538 A1 | 12/2013 | Harlev et al. |
| 2014/0024911 A1 | 1/2014 | Harlev et al. |
| 2014/0107508 A1 | 4/2014 | Harlev et al. |
| 2014/0200442 A1 | 7/2014 | Harlev et al. |
| 2014/0235986 A1 | 8/2014 | Harlev et al. |
| 2014/0275921 A1 | 9/2014 | Harlev et al. |
| 2014/0288451 A1 | 9/2014 | Brodnick et al. |
| 2015/0112178 A1 | 4/2015 | Harlev et al. |
| 2015/0150472 A1 | 6/2015 | Harlev et al. |
| 2015/0196217 A1 | 7/2015 | Harlev et al. |
| 2015/0223726 A1 | 8/2015 | Harlev et al. |
| 2015/0282729 A1 | 10/2015 | Harlev et al. |
| 2016/0000357 A1 | 1/2016 | Harlev et al. |
| 2016/0051160 A1 | 2/2016 | Harlev et al. |
| 2016/0051204 A1 | 2/2016 | Harlev et al. |
| 2016/0331259 A1 | 11/2016 | Harlev et al. |
| 2017/0042436 A1 | 2/2017 | Harlev et al. |
| 2017/0086705 A1 | 3/2017 | Harlev et al. |
| 2019/0038165 A1 | 2/2019 | Relan et al. |
| 2019/0216347 A1* | 7/2019 | Ghodrati ............. A61B 5/6858 |
| 2019/0365262 A1 | 12/2019 | Honicker |
| 2020/0214662 A1 | 7/2020 | Konofagou et al. |
| 2022/0054070 A1* | 2/2022 | Honarbakhsh ......... A61B 5/742 |

* cited by examiner

100

200

300

400

500

600

ELECTRICAL
SIGNAL'S
SOURCE
705

MAPPING
CATHETER
730.1

MAPPING
CATHETER
730.2

735

ENDOCARDIUM 710

740

500ms

500ms

A

TA=TR = 0ms
752

750.1

B

TB=
12ms

C

TC=
15ms

755

A

T750.2A=T750.1C=15ms 750.2

B

TB=
14ms

C

TC=
18ms

700

FIRST STAGE: 800A

SECOND STAGE: 800B

THIRD STAGE: 800C

800

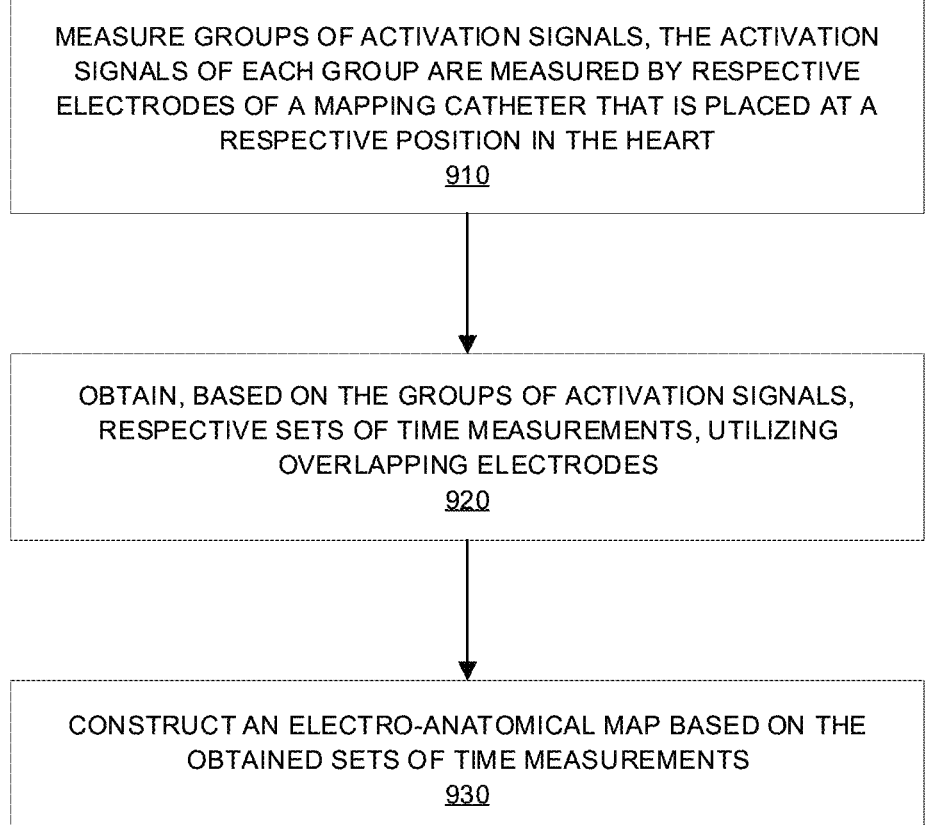

MEASURE GROUPS OF ACTIVATION SIGNALS, THE ACTIVATION
SIGNALS OF EACH GROUP ARE MEASURED BY RESPECTIVE
ELECTRODES OF A MAPPING CATHETER THAT IS PLACED AT A
RESPECTIVE POSITION IN THE HEART
910

OBTAIN, BASED ON THE GROUPS OF ACTIVATION SIGNALS,
RESPECTIVE SETS OF TIME MEASUREMENTS, UTILIZING
OVERLAPPING ELECTRODES
920

CONSTRUCT AN ELECTRO-ANATOMICAL MAP BASED ON THE
OBTAINED SETS OF TIME MEASUREMENTS
930

FIG. 9
900

ELECTRO-ANATOMICAL MAPPING WITHOUT ACQUIRING A REFERENCE SIGNAL

BACKGROUND

Three dimensional (3D) electro-anatomical maps of the heart are used to visualize cardiac tissue conduction and propagation of electrical signals across the endocardium. Activation signals (electrograms) may be acquired by a mapping catheter that measures those signals at various locations on the endocardium. To detect an activation time at a certain cardiac tissue location, an activation signal (measured at that location) is compared with a reference activation signal. Typically, a reference activation signal captures electrical activity generated by a source—e.g., the sinus node—by a dedicated reference catheter that is placed nearby that source—e.g., the coronary sinus (CS). However, in some patients, physicians are unable to insert a reference catheter into the CS. Furthermore, in some patients, inserting multiple catheters (e.g., the reference catheter, the mapping catheter, and, possibly, an ablation catheter) into the femoral vein anatomy proves to be challenging.

Furthermore, in some situations a reference catheter cannot be secured at one location, so that a moving spaciotemporal frame of reference can be prevented. In other situations, the myocardium, being measured by the reference catheter, may have electrical dissociation with the area being mapped, making the use of the reference catheter unhelpful in generating the 3D electro-anatomical map.

Hence, techniques are required for generating 3D electro-anatomical maps without the need to insert a reference catheter for the acquisition of a reference activation signal. Such techniques will allow for cardiac mapping using a single mapping catheter with a single access point to the heart.

BRIEF DESCRIPTION OF THE DRAWINGS

A more detailed understanding may be had from the following description, given by way of example in conjunction with the accompanying drawings, wherein like reference numerals in the figures indicate like elements, and wherein:

FIG. 9 is a flowchart of an example method for generating an electro-anatomical map of the heart, based on which one or more features of the disclosure may be implemented.

DETAILED DESCRIPTION

Figure 1:
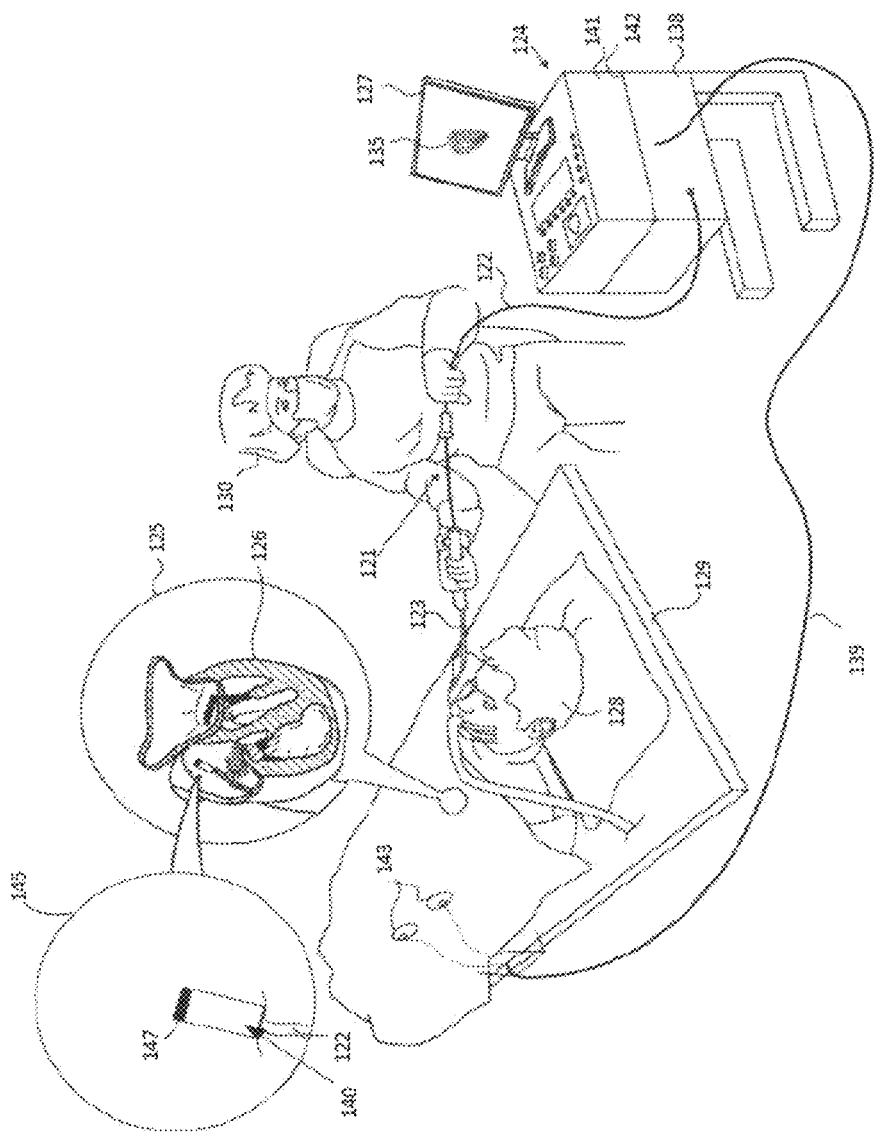
FIG. 1 is a diagram of an example cardiac mapping system, based on which one or more features of the disclosure may be implemented.

As disclosed herein, a multielectrode mapping catheter can be used to generate a 3D electro-anatomical map—such as a local arrival time (LAT) map of a chamber of the heart. This can be achieved without using an additional catheter for the acquisition of a reference activation signal. To that end, groups of activation signals may be acquired—a group of activation signals may be measured by the electrodes of a mapping catheter when placed at a respective location on the endocardium. Then, sets of time measurements can be derived from respective groups of activation signals. Time measurements of one set are related to time measurements of another set through measurements in those two sets that correspond to activation signals that were measured by spatially overlapping electrodes. Aspects of the 3D electro-anatomical mapping described herein can be performed by a cardiac mapping system such as the CARTO®3 3D system. Generally, a cardiac mapping system can provide 3D visualization of the heart anatomy overlaid, for example, with a LAT map that visualizes electrical properties of the heart. A mapping system that may be utilized to employ aspects of the 3D electro-anatomical mapping is described in reference to FIGS. 1-5.

Aspects of the present disclosure describe methods for generating an electro-anatomical map of the heart. The methods comprise measuring groups of activation signals. The activation signals of each group are measured by respective electrodes of a mapping catheter that is placed at a respective position in the heart, wherein at least one electrode of the mapping catheter that measured an activation signal of one group of the groups spatially overlapped with a respective electrode of the mapping catheter that measured an activation signal of another group of the groups. The methods further comprise obtaining, based on the groups of activation signals, respective sets of time measurements, utilizing the overlapping electrodes. And, then, constructing, based on the obtained sets of time measurements, the electro-anatomical map.

Aspects of the present disclosure also describe systems for generating an electro-anatomical map of the heart. The systems comprise at least one processor and memory storing instructions. The instructions, when executed by the at least one processor, cause the systems to measure groups of activation signals. The activation signals of each group are measured by respective electrodes of a mapping catheter that is placed at a respective position in the heart, wherein at least one electrode of the mapping catheter that measured an activation signal of one group of the groups spatially overlapped with a respective electrode of the mapping catheter that measured an activation signal of another group of the groups. The instructions further cause the systems to obtain, based on the groups of activation signals, respective sets of time measurements, utilizing the overlapping electrodes, and, then, to construct, based on the obtained sets of time measurements, the electro-anatomical map.

Furthermore, aspects of the present disclosure describe a non-transitory computer-readable medium comprising instructions executable by at least one processor to perform methods for generating an electro-anatomical map of the heart. The methods comprise measuring groups of activation signals. The activation signals of each group are measured by respective electrodes of a mapping catheter that is placed at a respective position in the heart, wherein at least one electrode of the mapping catheter that measured an activation signal of one group of the groups spatially overlapped with a respective electrode of the mapping catheter that measured an activation signal of another group of the groups. The methods further comprise obtaining, based on the groups of activation signals, respective sets of time measurements, utilizing the overlapping electrodes. And, then, constructing, based on the obtained sets of time measurements, the electro-anatomical map.

FIG. 1 is a diagram of an example cardiac mapping system 100, based on which one or more features of the disclosure may be implemented. The system 100 may include a console 124, a display 127, and a catheter 140, operated by a user (e.g., a physician or a medical professional) 130. The system 100 may be configured to obtain anatomical and electrical measurements, taken from an organ of a patient 128 such as the heart 126, to visualize the obtained anatomical and electrical measurements, and to perform a cardiac ablation procedure. Inset 145 shows the catheter 140 in an enlarged view and inset 125 shows the catheter 140 inside a cardiac chamber of the heart 120. An example of system 100 is the CARTO® 3 3D mapping system of Biosense Webster.

The catheter 140 shown in FIG. 1 is representative herein of one or more catheters that may be employed by the system 100, including an ablation catheter and a mapping catheter. An ablation catheter may be configured to damage (ablate) tissue areas of an intra-body organ. A mapping catheter, equipped with one or more electrodes, may be configured to obtain biometric data including electric signals. The system 100 may include one or more probes 121, having shafts 122 that may be navigated by a physician 130 into a body part, such as the heart 126, of a patient 128 lying on a table 129. The physician 130 may insert a shaft 122 through a sheath 123, while manipulating the distal end of the shafts 122 using a manipulator near the proximal end of the catheter 140 and/or while deflecting from the sheath 123. As shown 145, the catheter 140 may be fitted at the distal end of the shaft 122. The catheter 140 may be inserted through the sheath 123 in a collapsed state and may then be expanded within the heart 126.

In an aspect, electrical properties of the heart (e.g., biometric data derived from electrical signals acquired by catheters' electrodes) may represent information associated with a LAT, an electrical activity, a topology, a unipolar or a bipolar voltage, a dominant frequency, or an impedance, for example. A LAT may represent a time at which an electrical activity has been measured at a certain location. The LAT may be calculated based on a normalized initial starting point that may be derived from a reference catheter. An electrical activity may be any applicable electrical signal that may be measured based on one or more thresholds. The electrical activity may be augmented (e.g., using filters to improve the signal to noise ratios). A topology may represent the physical structure of a body part or a portion of a body part or may correspond to changes in the physical structure between different portions of the body part or between different body parts. A dominant frequency may represent a frequency, or a range of frequencies, that is prevalent in a portion of a body part and may be different in different portions of the same body part. For example, the dominant frequency of a pulmonary vein in the heart may be different from the dominant frequency of the right atrium of the same heart. An impedance may represent resistance at a given area of a body part.

The console 124 of the system 100 may include a processing unit 141, memory 142, and communications interface circuitry 138. The processing unit 141 may be a computer equipped with a multi-core processor and may comprise a front end and control components. The memory 142 may comprise volatile and/or non-volatile memory. The communications interface circuitry 138 may be used for transmitting and receiving signals to and from the catheter 140. The console 124 may be configured to receive biometric data, and then, to process, to visualize, and to store the biometric data for later processing, or to transmit the data to another system via a network. In an aspect, the processing unit 141 may be external to the console 124 and may be located, for example, in the catheter 140, in an external device, in a mobile device, in a cloud-based device, or may be a standalone processor. The processing unit 141 may execute software modules programed to carry out the functions of aspects described herein. The software modules may be downloaded to the processing unit 141 over a network or from non-transitory tangible media, such as magnetic, optical, or electronic memory, external or local to the console 124.

The system 100 may be modified to implement aspects disclosed herein. Aspects disclosed herein may be similarly applied using other system components and settings. Additionally, the system 100 may include additional components, such as elements for sensing electrical activity, wired or wireless connectors, processing units, or display devices. The console 124 may include real-time noise reduction circuitry typically configured as a field programmable gate array (FPGA), followed by an analog-to-digital (A/D) ECG (electrocardiograph) or EMG (electromyogram) signal conversion integrated circuit. The output of the A/D ECG or EMG circuit may be processed to perform methods disclosed herein.

The console 124 may be connected, by a cable 139, to body surface electrodes 143, which may include adhesive skin patches that are affixed to the patient 128. The processing unit 141, in conjunction with a tracking module, may determine position coordinates of the catheter 140 inside a body part (e.g., the heart 126) of the patient 128. The position coordinates may be based on impedances or electromagnetic fields measured between the body surface electrodes 143 and electrodes (or other electromagnetic components) of the catheter 140. Additionally, or alternatively, the position coordinates may be based on impedances or electromagnetic fields measured between location pads attached to the surface of the bed 129 and electrodes (or other electromagnetic components) of the catheter 140.

During a procedure, the processing unit 141 may facilitate the rendering 135 of a body part 126 on the display 127 to be viewed by the physician 130 and may store data representing the body part in the memory 142. In an aspect, the physician 130 may be able to rotate and move the rendered body part 135 (e.g., change the point of view of the rendered body part) using one or more input devices, such as a touchscreen, a touch pad, a mouse, a keyboard or a gesture recognition apparatus. For example, the position of the catheter 140 may be change to collect measurements based on which the rendering 135 of a body part 126 is updated. Additionally, a representation of the catheter may be rendered in relation to the rendering of the body part, to allow the physician 130 to better navigate the catheter within the body part. In an aspect, the display 127 may be located at a remote location such as a separate hospital or in separate healthcare provider networks.

Figure 2:
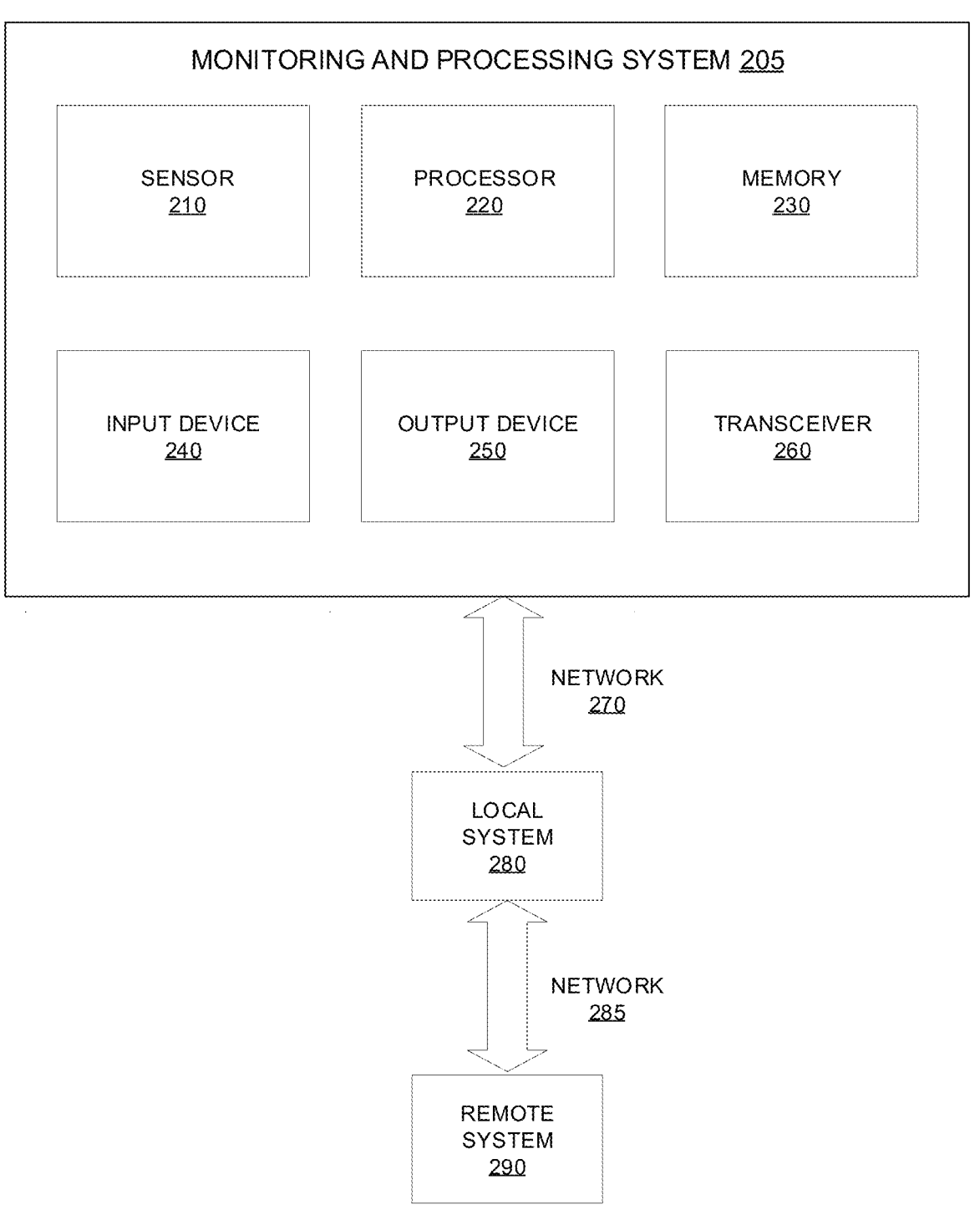
FIG. 2 is a block diagram of an example system, deployable by the example cardiac mapping system of FIG. 1, based on which one or more features of the disclosure may be implemented.

FIG. 2 is a block diagram of an example system 200, deployable by the example cardiac mapping system 100 of FIG. 1, based on which one or more features of the disclosure may be implemented. The system 200 may include a monitoring and processing system 205, a local system 280, and a remote system 290. The monitoring and processing system 205 may include a sensor 210, a processor 220, memory 230, an input device 240, an output device 250, and a transceiver 260, e.g., a transmitter-receiver in communication with a network 270. The system 205 may continually or periodically monitor, store, process, and communicate, via the network 270, various patient biometric data. Patient biometric data may include electrical signals (e.g., ECG signals), anatomical images, blood pressure data, blood glucose data, and temperature data, for example. The patient biometric data may be monitored (processed, visualized, communicated) to facilitate treatment of various diseases, such as cardiovascular diseases (e.g., arrhythmias, cardiomyopathy, and coronary artery disease) and autoimmune diseases (e.g., type I and type II diabetes).

In an aspect, the monitoring and processing system 205 may represent the console 124 of the system 100 shown in FIG. 1. In another aspect, the monitoring and processing system 205 may be internal to the patient's body—e.g., the system 205 may be subcutaneously implantable, inserted orally or surgically, via a vein or an artery, via an endoscopic or a laparoscopic procedure. In yet another aspect, the system 205 may be externally attached to the patient's skin. Alternatively, the system 205 may include components that are internal to the patient's body and components that are external to the patient's body.

The monitoring and processing system 205, may represent a plurality of monitoring and processing systems 205 that may process biometric data of a patient in parallel, in communication with each other and/or in communication with a server via a network. One or more systems 205 may acquire or receive all or part of a patient's biometric data (e.g., electrical signals, anatomical images, blood pressure, temperature, blood glucose level, or other biometric data). The one or more systems 205 may also acquire or receive additional information associated with the acquired or received patient's biometric data from one or more other systems 205. The additional information may be, for example, diagnosis information and/or information obtained from a device such as a wearable device. Each monitoring and processing system 205 may process data acquired by it and may process data received from another system 205.

The sensor 210 may represent one or more sensors that may be configured to sense biometric data from a patient. For example, the sensor 210 may be an electrode configured to acquire electrical signals (e.g., bioelectrical signals originating in the heart), a temperature sensor, a blood pressure sensor, a blood glucose sensor, a blood oxygen sensor, a pH sensor, an accelerometer, or a microphone. In an aspect, system 205 may comprise an ECG monitoring system that measures ECG signals originating in the heart. In such a case, the sensor 210 may include one or more electrodes that may be configured to acquire the ECG signals. The ECG signals may be used to diagnose and treat various cardiovascular diseases. In an aspect, the sensor 210 may include a catheter with one or more electrodes, a probe, a blood pressure cuff, a weight scale, a bracelet (e.g., a smart watch biometric tracker), a glucose monitor, a continuous positive airway pressure (CPAP) machine, or any other device that provides biometric data or other data concerning the patient's health.

The transceiver 260 may include a transmitter component and a receiver component. These transmitter component and receiver component may be integrated into a single device or separately implemented. The transceiver may provide connectivity between the system 205 and other systems or servers via a communication network 270. The network 270 may be a wired network, a wireless network or include a combination of wired and/or wireless networks. The network 270 may be a short-range network (e.g., a local area network (LAN) or a personal area network (PAN)). Information may be sent or may be received via the short-range network using various short-range communication protocols such as Bluetooth, Wi-Fi, Zigbee, Z-Wave, near field communications (NFC), ultra-band, or infrared (IR). The network 270 may also be a long-range network (e.g., wide area network (WAN), the internet, or a cellular network). Information may be sent or may be received via the long-range network using various long-range communication protocols such as TCP/IP, HTTP, 3G, 4G/LTE, or 5G/New Radio.

The processor 220 may be configured to process patient's biometric data, for example, obtained by the sensor 210, and store the biometric data and/or the processed biometric data in memory 230. The processor 220 may also be configured to communicate the biometric data across the network 270 via a transmitter of the transceiver 260. Biometric data from one or more other monitoring and processing systems 205 may be received by a receiver of the transceiver 260. The processor 220 may employ algorithms (e.g., artificial-intelligence-based algorithms such as machine learning algorithms), or, alternatively or in addition, algorithms may be employed by other processors (e.g., at the local system 280 or the remote system 290). In aspects, the processor 220 may include one or multiple CPUs, one or multiple GPUs, or one or multiple FPGAs. In these aspects, the algorithms may be executed on one or more of these processing units. Similarly, the processor 220 may include an ASIC dedicated to performing deep learning calculations (such as the Intel® Nervana™ Neural Network Processor) and machine learning algorithms may be executed on such dedicated ASIC. The processing unit that executes the algorithms may be located in the medical procedure room or in another location (e.g., another medical facility or a cloud).

The input device 240 of the monitoring and processing system 205 may be used as a user interface. The input device 240 may include, for example, a piezoelectric sensor or a capacitive sensor that is configured to receive user input, such as tapping or touching. Hence, the input device 240 may be configured to implement capacitive coupling in response to tapping or touching a surface of the system 205 by a user. Gesture recognition may be implemented by various capacitive coupling such as resistive capacitive, surface capacitive, projected capacitive, surface acoustic wave, piezoelectric, or infra-red touching. Capacitive sensors may be placed on the surface of the input device 240 so that the tapping or touching of the surface activates the system 205. The processor 220 may be configured to respond selectively to different tapping patterns of the capacitive sensor (e.g., a single tap or a double tap on the input device 240) such that different functions of the system 205 (e.g., acquisition, storing, or transmission of data) may be activated based on the detected pattern. In an aspect, audible feedback may be given to the user from the system 205, e.g., when a gesture is detected and recognized.

The local system 280, that may be in communication with the monitoring and processing system 205 via the network 270, may be configured to act as a gateway to the remote system 290 through another network 285 that may be accessible to the local system 280. The local system 280 may be, for example, a smart phone, smartwatch, tablet, or other portable smart device. Alternatively, the local system 280 may be a stationary or a standalone device. Patient biometric data may be communicated between the local system 280 and the monitoring and processing system 205. In an aspect, the local system 280 may also be configured to display the acquired patient biometric data and associated information.

The remote system 290 may be configured to receive at least part of the monitored patient biometric data and associated information via the network 285, which may be a long-range network. For example, if the local system 280 is a mobile phone, network 285 may be a wireless cellular network, and information may be communicated between the local system 280 and the remote system 290 via a wireless technology standard, such as any of the wireless technologies mentioned above. The remote system 290 may be configured to present received patient biometric data and the associated information to a healthcare professional (e.g., a physician), either visually on a display or aurally through a speaker.

Figure 3:
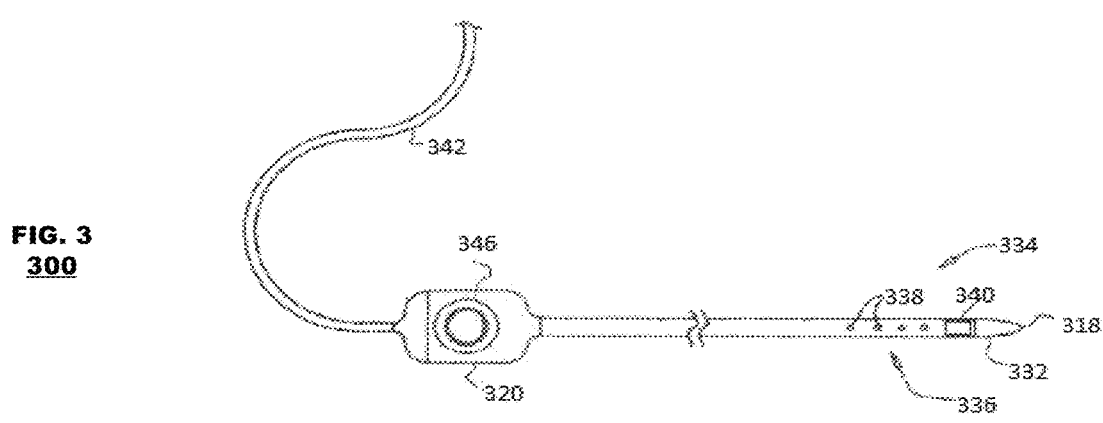
FIG. 3 illustrates an example catheter, based on which one or more features of the disclosure may be implemented.
Figure 4:
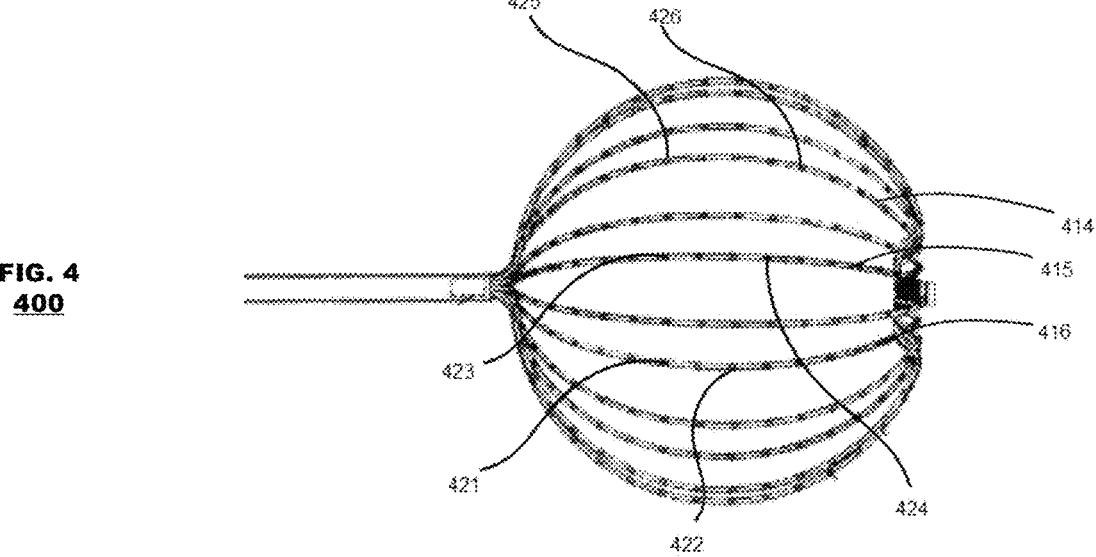
FIG. 4 illustrates an example balloon catheter, based on which one or more features of the disclosure may be implemented.
Figure 5:
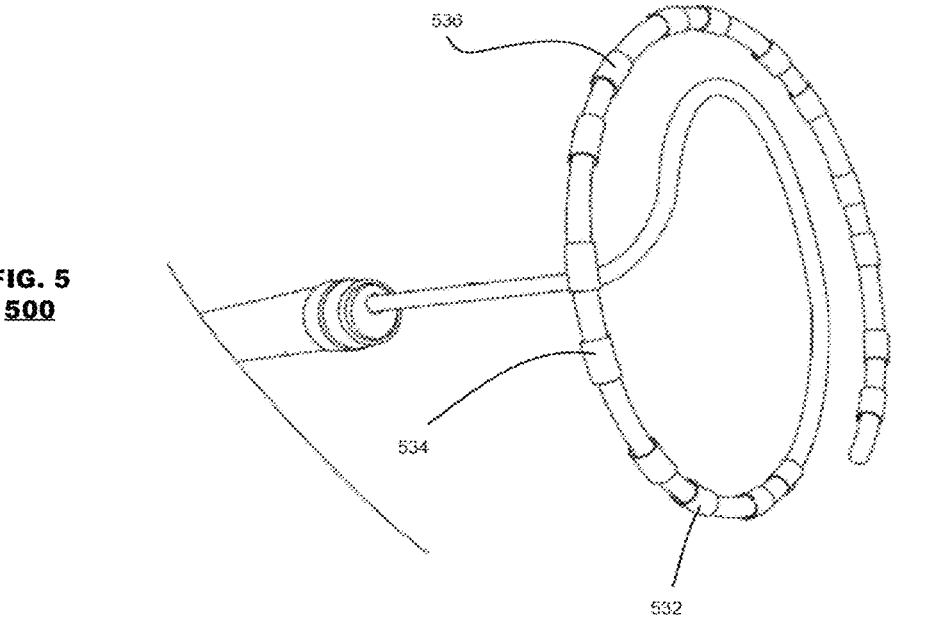
FIG. 5 illustrates an example loop catheter, based on which one or more features of the disclosure may be implemented.

FIGS. 3, 4, and 5 illustrate, respectively, example catheters 300, 400, 500. Electrodes or sensors, disposed on the distal portion of the catheters 300, 400, 500, may be used to obtain electrical signals measured at the heart tissue that may be used for anatomical and electrical mapping. Another multielectrode mapping catheter that is commonly used is a Pentaray® catheter (not shown). As mentioned above, an additional catheter may be used to acquire a reference signal. Such a reference signal can be used to temporally relate signals acquired, for example, by a Pentaray® catheter or a balloon catheter 400. Other electrodes or sensors may be used to emit electrical signals into the heart tissue, for example, for therapeutic purposes (ablation) and/or to facilitate catheter localization.

FIG. 3 illustrates a catheter 300 that include a contact electrode 332 and non-contact electrodes 338. The non-contact electrodes may measure far-field electrical signals in the heart chamber and may be arranged in an array 336 along the longitudinal axis of a distal portion 334 of the catheter 300. The distal portion 334 may further include a position sensor 340 (or multiple position sensors) that can generate or measure signals used to determine the sensor's 340 position and orientation. As there is a fixed spatial relation between the position sensor 340 and the distal tip 318 and other electrodes 332, 338, the positions of the distal tip 318 and the other electrodes 332, 338 can be resolved based on the determined position of the position sensors 340. The handle 320 of the catheter 300 may include controls 346 to steer or deflect the distal portion 334, or to orient it as desired.

For example, the position sensor 340 may be configured to sense an electrical field that may be produced by the system 100, 200 (for sensor localization purposes) and to transmit signals generated from the sensed field over a cable 342 running through the catheter 300 to the console 124 (that is, cable 122 shown in FIG. 1). In another alternative, the position sensor 340 may transmit the signals to the console 124 over a wireless link. Based on the signals sent by the position sensor 340, the processing unit 141, 220 may calculate the location and the orientation of the distal portion 334 of the catheter 300 as well as the location and the orientation of the distal tip 318 and the other electrodes 332, 338. The location and the orientation calculations may be carried out based on the signals sent by the position sensor 340 after those signals were amplified, filtered, digitized, or otherwise processed by the system 100, 200.

To acquire electrical activity at a point in the heart, a catheter 300 may be advanced into the heart and its distal tip 318 may be brought in contact with the endocardium at a certain tissue location to acquire data at that location. To construct an anatomical and electrical map of the heart, this data acquisition process has to be repeated for a large number of locations within a region of interest. Constructing a detailed map of a region of interest in the heart via such a point-by-point data accumulation process may take a long period of time. To address this shortcoming, multiple-electrode catheters have been developed to simultaneously measure electrical activity at multiple location points in the heart. Multielectrode catheters may be implemented using any applicable shape such as a balloon catheter (described in reference to FIG. 4) or a loop catheter (described in reference to FIG. 5).

FIG. 4 illustrates an example balloon catheter 400, based on which one or more features of the disclosure may be implemented. As shown in FIG. 4, a balloon catheter 400 may include multiple splines, such as splines 414, 415, 416. Multiple electrodes are disposed on each spline, such as electrodes 421-426, shown in FIG. 4. The balloon catheter 400 may be designed such that when deployed into a patient's body, its electrodes may be held in close contact against an endocardial surface. For example, a balloon catheter may be inserted into a lumen, such as a pulmonary vein. The balloon catheter may be inserted into the pulmonary vein in a deflated state such that the balloon catheter does not occupy its maximum volume while being inserted. The balloon catheter may then be expanded while inside the pulmonary vein such that the electrodes on the balloon catheter come into contact with an entire circular section of the pulmonary vein. Such contact with an entire circular section of the pulmonary vein, or any other lumen, may enable measurement of the electrical activity from multiple points on the tissue. That is, each acquisition may result in as many activation signals as the number of electrodes.

FIG. 5 illustrates an example loop catheter 500, based on which one or more features of the disclosure may be implemented. A loop catheter 500 (also referred to as a lasso catheter) may include multiple electrodes 532, 534, 536 that when brought in contact with the heart tissue (endocardial wall) may simultaneously acquire electrical signals measured at the locations of the electrodes. A loop catheter 500 may be fully or partially elastic such that it can twist, bend, and or otherwise change its shape based on a received signal and/or based on the application of an external force (e.g., when pushed against cardiac tissue).

Hence, a multielectrode catheter (such as a Pentaray® catheter, a balloon catheter 400, or a loop catheter 500) may be advanced into a chamber of the heart to acquire electrical (activation) signals. Position sensors disposed on the multielectrode catheter (at a known spatial relation to the electrodes) may be used by the system 100, 200 to establish the locations in the heart of each of the electrodes. The electrical signals that are measured by each electrode may be recorded and may be presented to a physician on the display 127 by the system 100, 200. For example, the measured electrical signals may be presented as vertically aligned electrograms that are temporally correlated according to a reference signal. Typically, the reference signal is measured by a dedicated reference electrode that may be placed, for example, at the CS. Thus, when using a multielectrode catheter that is equipped with many electrodes (each electrode being positioned on the endocardial surface) the physician may collect activation signals as many as the number of electrodes.

Figure 6:
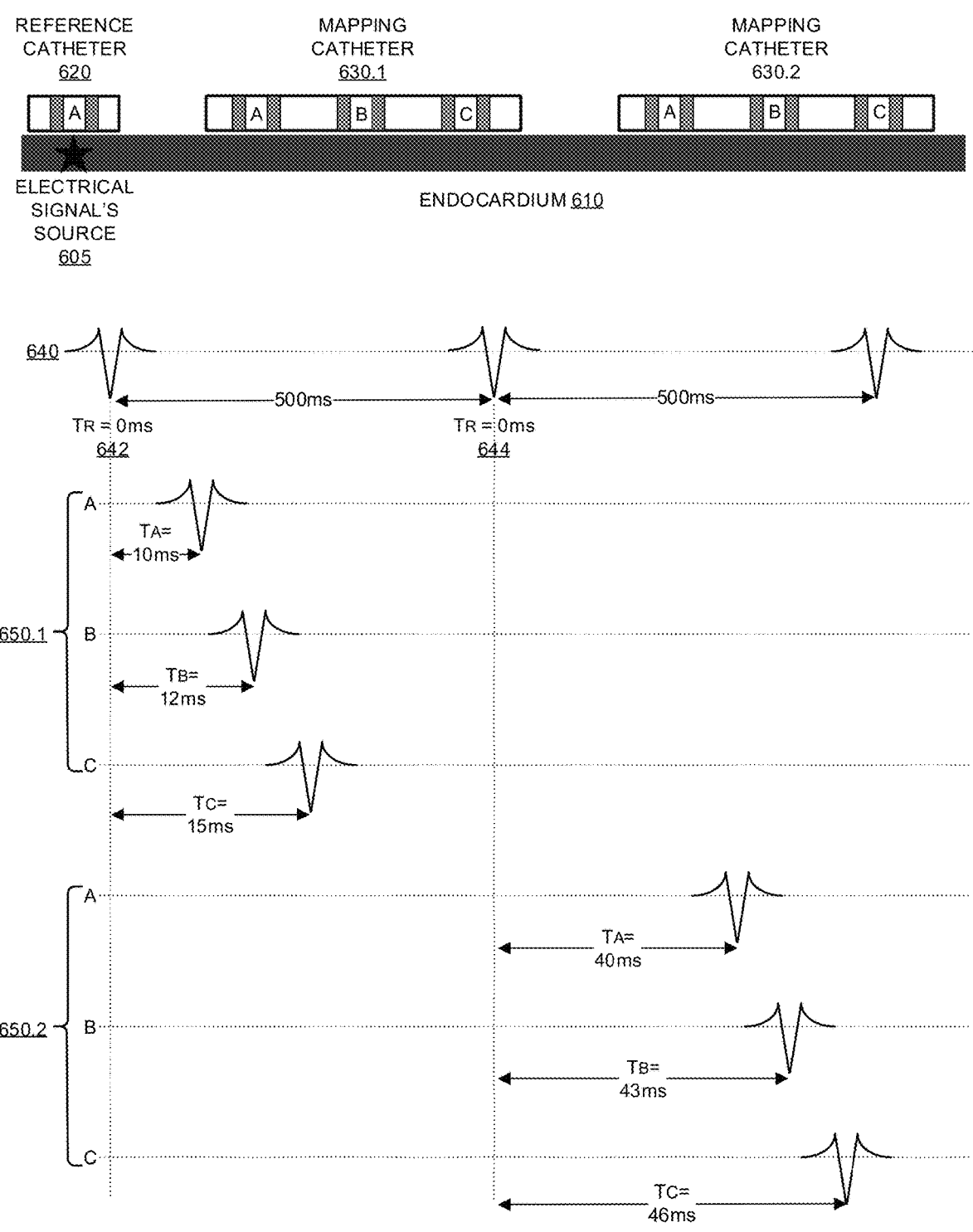
FIG. 6 illustrates an example method for electro-anatomical mapping using a mapping catheter and a reference catheter, based on which one or more features of the disclosure may be implemented.

FIG. 6 illustrates an example method 600 for electro-anatomical mapping using a multi-electrode mapping catheter 630 and a reference catheter 620, based on which one or more features of the disclosure may be implemented. In the example shown in FIG. 6, the catheters 620, 630 are equipped with pairs of electrodes 620A, 630A, 630B, 630C—each pair is configured to measure a bipolar beat. Aspects described herein can be applied also when employing non-paired electrodes where each electrode is configured to measure a unipolar beat. As demonstrated, the mapping catheter 630 is placed at a first location 630.1 on the endocardium 610, and, then, is moved to a second location 630.2 on the endocardium. Thus, the mapping catheter 630, when placed at different locations on the endocardium, measures activation signals at those respective locations. That is, at each location, a pair of electrodes measure the depolarization of the tissue at that location—depolarization that is caused by an electrical signal 605 that propagates through the endocardium 610. The electrical signal 605 may originate at the sinus node (e.g., when caused by a normal heart beat) or may originate at any other location (e.g., when caused by tachycardia or a pacing catheter). The reference catheter 620 is typically used to measure activation at a tissue location nearby the origin of the electrical signal 605. For example, when the electrical signal 605 originates at the sinus node, the reference catheter 620 may acquire a signal 640 with a normal heart beat that appears every ~500 milliseconds (ms).

To construct an electro-anatomical map, time measurements associated with the activation (or depolarization) of the tissue at various locations on the endocardium have to be collected and temporally related to each other. This is traditionally done by measuring activation signals while moving the mapping catheter along the cardiac tissue of one of the heart's chambers. For example, a first group of activation signals 650.1 may be measured by the electrodes of the mapping catheter 630.1 when positioned at a first location and a second group of activation signals 650.2 may be measured by the electrodes of the mapping catheter 630.2 when positioned at a second location. As shown in FIG. 6, each group may include activation signals A, B, and C (e.g., of group 650.1) that were measured by respective pairs of electrodes A, B, and C (e.g., acquired at the first location of the mapping catheter 630.1). To construct a LAT map, sets of time measurements are derived from respective groups of activation signals. For example, the set of time measurements $T_A$=10 ms, $T_B$=12 ms, and $T_C$=15 ms are derived, respectively, from group 650.1 of activation signals A, B, and C. And, the set of time measurements $T_A$=40 ms, $T_B$=43 ms, and $T_C$=46 ms are derived, respectively, from group 650.2 of activation signals A, B, and C. As illustrated, these time measurements are derived relative to the beats of the reference signal 640 (acquired by the reference catheter 620) using a reference time $T_R$=0 ms 642, 644. In this way, measurements in one set (e.g., 650.1-$T_A$, 650.1-$T_B$, and 650.1-$T_C$) can be combined with measurements in a second set (e.g., 650.2-$T_A$, 650.2-$T_B$, and 650.2-$T_C$) to form one map that visualizes the electrical signal propagation across the walls of a cardiac structure (e.g., the left ventricular). However, as stated above, the need to use a reference catheter 620 complicates the mapping procedure (and in some patients is not feasible). A method for mapping that does not require the use of a reference catheter 620 is described next with reference to FIGS. 7-9.

Figure 7:
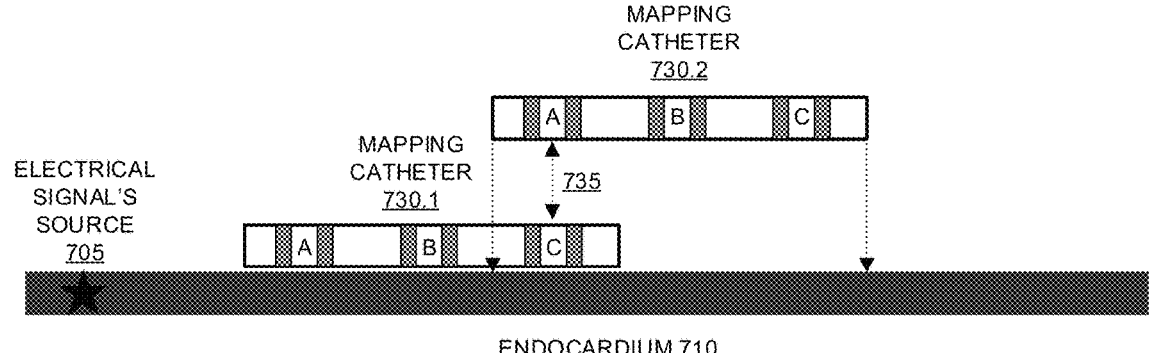
FIG. 7 illustrates an example method for electro-anatomical mapping using a mapping catheter, based on which one or more features of the disclosure may be implemented.

FIG. 7 illustrates an example method 700 for electro-anatomical mapping using a multi-electrode mapping catheter, based on which one or more features of the disclosure may be implemented. As illustrated, an electrical signal 705 (the equivalent of signal 605) activates the endocardium 710. The activation at a tissue location nearby the origin of the electrical signal 705 is shown by activation signal 740. However, in contrast to the method 600 described in reference to FIG. 6, there is no need to acquire this signal 740 by a reference catheter (such as catheter 620) because this signal 740 is not required to be used as a reference according to this method 700, as further described below.

As illustrated in FIG. 7, during a mapping procedure, the mapping catheter 730 is moved from a first location 730.1 to a second location 730.2, so that at least one spatial overlap exists between electrodes. That is, in the example of FIG. 7, when the mapping catheter is placed at the second location 730.2, the electrode pair A is located at the same location 735 at which the electrode pair C was located when the catheter was placed at the first location 730.1. Accordingly, the activation signal C (of group 750.1) and the activation signal A (of group 750.2) can be associated 755. That is, their respective time measurements can be assumed to be the same. Hence, time measurements from multiple sets may be temporally related due to the spatial overlap between electrode pairs (or electrodes when unipolar signals are measured) without the use of a reference signal 740. For example, activation signal A of group 750.1 can be used as a reference 752: $T_A$=$T_R$=0 ms. The other time measurements associated with group 750.1 can be measured relative to that reference—thus, as illustrated, $T_B$=12 ms and $T_C$=15 ms. Next, with respect to time measurements of group 750.2, since activation signal C (of group 750.1) and activation signal A (of group 750.2) are measured by spatially overlapping electrode pairs (respectively, electrode pair C of 730.1 and electrode pair A of 730.2), their time measurements are assumed to be sufficiently close—that is, 15 ms. Using this assumption, time measurements of group 750.2 can be related to time measurements of group 750.1. Accordingly, as illustrated, the time measurements associated with group 750.2 are $T_A$=15 ms, $T_B$=14 ms+15 ms=29 ms, and $T_C$=18 ms+15 ms=23 ms. Note that the roles of the groups 750.1 and 750.2, as described above, can be switched and any one of the activation signals of a group (750.1 or 750.2) may be used as a reference $T_R$.

In this manner, time measurements from multiple sets (associated with respective groups of activation signals) can be related—or, in other words, time measurement sets (corresponding to different mapping catheter positions on the endocardium) may be combined—as long as each group of activation signals (associated with each set of time measurements) includes at least one activation signal that was measured by an electrode that overlapped with another electrode that measured an activation signal of another group. Aspects of method 700 are further described in reference to FIG. 8.

Figure 8:
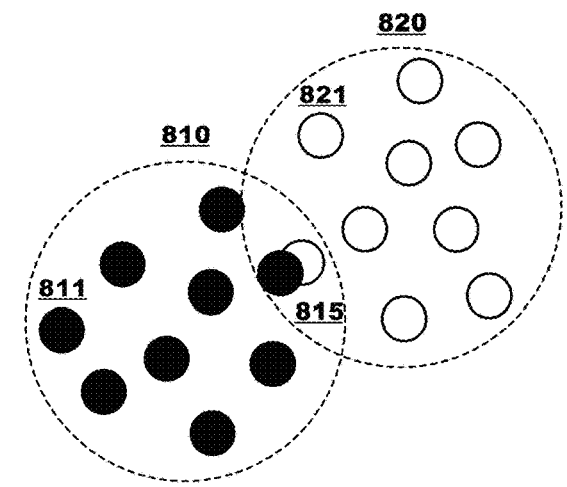
FIG. 8 illustrates an example method for combining sets of measurements acquired by a mapping catheter, based on which one or more features of the disclosure may be implemented.
Figure 8:
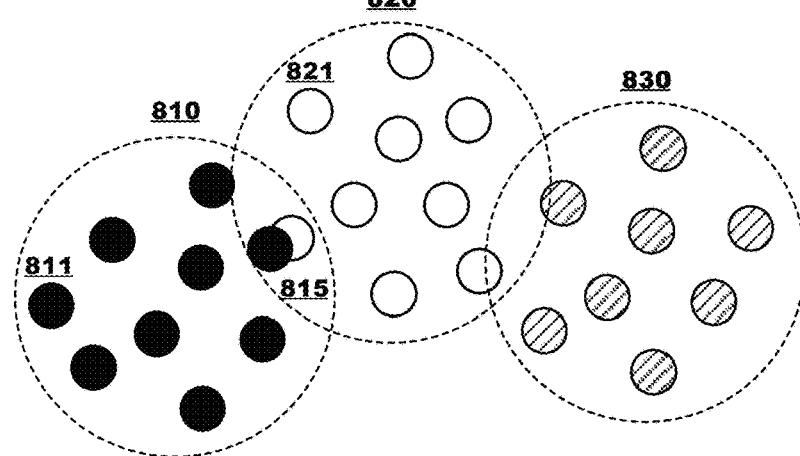
Figure 8:
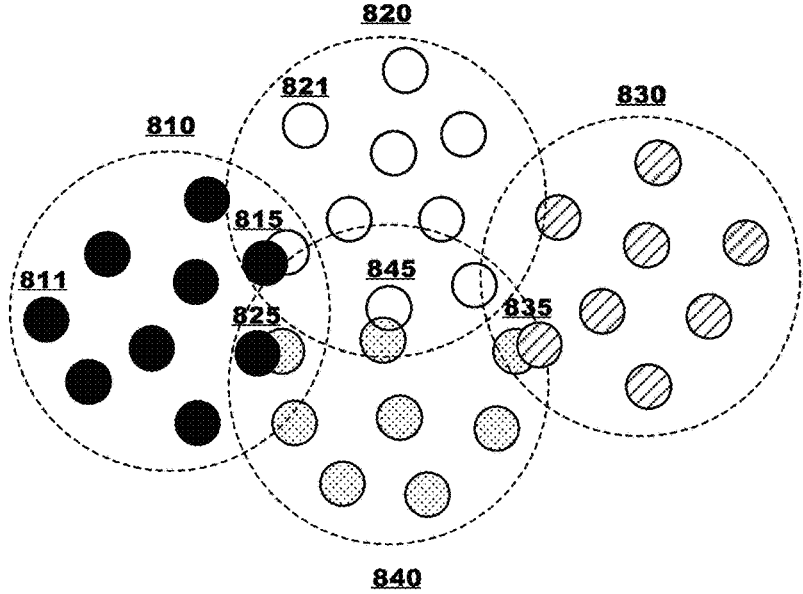

FIG. 8 illustrates an example method 800 for combining sets of measurements acquired by a mapping catheter, based on which one or more features of the disclosure may be implemented. The concepts demonstrated in FIG. 8 are similar to those demonstrated in FIG. 7, however, in FIG. 8 the locations of the mapping catheter's electrodes (or pairs of electrodes in the bipolar case) are shown in a two-dimensional (2D) space. The same concepts, as described herein, apply to electrodes' locations in a 3D space, as is the case in practice when using, for example, a multielectrode mapping catheter such as a Pentaray® catheter or the catheters shown in FIGS. 4-5.

During a mapping procedure, a physician moves the mapping catheter from one position on the cardiac tissue to another. At each position, the catheter's electrodes acquire activation signals from which a set of time measurements can be obtained. Thus, each time measurement set corresponds to each positioning of the mapping catheter during the mapping procedure. FIG. 8 demonstrates four sets of time measurements 810, 820, 830, 840. A first set 810 of measurements was obtained from activation signals measured by electrodes at locations represented by solid circles and acquired when the catheter was placed in a first position. A second set 820 of measurements was obtained from activation signals measured by electrodes at locations represented by hollow circles and acquired when the catheter was placed in a second position. A third set 830 of measurements was obtained from activation signals measured by electrodes at locations represented by diagonally patterned circles and acquired when the catheter was placed in a third position. And, a fourth set 840 of measurements was obtained from activation signals measured by electrodes at locations represented by dotted circles and acquired when the catheter was placed in a fourth position.

As explained with respect to the time measurement sets of respective groups 750.1, 750.2 of FIG. 7, the four sets 810, 820, 830, 840 of time measurements can be combined. For example, the sets can be combined in stages as they are obtained from activation signals acquired by the mapping catheter as it moves along the endocardium. Starting with set 810, for example, an activation signal that was measured at electrode location 811 may be selected to provide a time-reference $T_R$ (e.g., such as the reference 750.1-$T_A$ 752 of FIG. 7). Relative to that time-reference, the time measurements associated with activation signals that were measured at the other electrode locations of set 810 are computed (e.g., just as time measurements 750.1-$T_B$ and 750.1-$T_C$ of FIG. 7 were computed). The time measurements associated with activation signals that were measured at electrode locations of the other sets 820-840, are computed based on overlapping electrodes (e.g., just as time measurements 750.2-$T_A$, 750.2-$T_B$ and 750.2-$T_C$ of FIG. 7 were computed). Combining the measurement sets 810-840 may be done in stages as is demonstrated next.

In a first stage of the mapping procedure 800A, activation signals may be measured by electrodes of the second set 820. The time measurements of this set 820 may be obtained by combining it 820 with set 810, utilizing a first spatial overlap 815 that exists between respective electrodes of the sets 810, 820. Then, in a second stage of the mapping procedure 800B, activation signals may be measured by electrodes of the third set 830. This set 830 cannot be combined with either of the previous sets 810, 820 since there is no spatial overlap between any electrode of set 830 and any electrode of the other two sets 810, 820. However, in a third stage of the mapping procedure 800C, where activation signals may be measured by electrodes of the fourth set 840, additional spatial overlaps can be introduced. For example, a second spatial overlap 825 between respective electrodes from sets 810 and 840, a third spatial overlap 835 between respective electrodes from sets 830 and 840, and a fourth spatial overlap 845 between respective electrodes from sets 820 and 840. Hence, the time measurements of set 840 can be obtained by combining it with set 810, set 820, or set 830, utilizing the spatial overlaps 825, 845, or 835, respectively. Moreover, at this stage 800C, the time measurements of set 830 can be obtained by combining it

830 with set 840, utilizing the third spatial overlap 835. In this manner, more measurement sets can be combined and a LAT map can be constructed based on these sets' time measurements.

In practice, and as illustrated in FIG. 8, the spatial overlaps 815, 825, 835, 845 between electrodes may not be perfect. That is, the spatial distance between the overlapping electrodes is not likely to be zero. And, thus, the time measurements that are computed based on those overlaps may embed errors. Such errors may be accumulative as time measurements of one set rely on the computation of time measurements of another set. One way to reduce the error is to take under consideration the degree of overlap. For example, as shown, set 840 includes three overlapping electrodes 825, 835, and 845. And so, in an aspect, based on the degree of overlap, time measurements of set 840, can be computed based on overlap 825, denoted $T_{825}$, based on overlap 835, denoted $T_{835}$, or based on overlap 845, denoted $T_{845}$. In another aspect, the time measurements of set 840 may be computed based on a weighted combination as follows:

$$T(S=840)=\omega_{825}\cdot T_{825}(S)+\omega_{835}\cdot T_{835}(S)+\omega_{845}\cdot T_{845}(S), \quad (1)$$

where, T(S) represents the time measurements of set S, and the weights $\omega_{825}$, $\omega_{835}$, $\omega_{845}$ are proportional to the degree of overlap in respective spatial overlaps 825, 835, and 845. The degree of overlap may be determined based on the distance between the locations of the overlapping electrodes. For example, a distance below a first threshold (typically, limited by the accuracy of the system in locating the electrodes) may correspond to 100% overlap, while a distance above a second threshold (typically, a function of the spatial distances among electrodes in the mapping catheter) may result in a 0% overlap.

In an aspect, M versions of time measurements of N number of sets can be computed $T_{i=1-M}=\{T_i(S):S=1-N\}$. Each version $T_i$ may be computed based on a different order in which the sets (e.g., sets 810, 820, 830, and 840) are combined. Alternatively, or in combination, each version $T_i$ may be computed based on a different reference time $T_R$ (e.g., a reference time associated with electrode 811 or 821). Alternatively, or in combination, each version $T_i$ may use a different scheme to compute the time measurements with respect to a set $T_i(S)$, as explained above, for example, with respect to equation (1). Time measurements that are associated with an electrode at a certain location x may then be extracted from all the M versions, denoted $\{T_i(x):i=1-M\}$. And, the time measurement associated with an electrode at location x, T(x), may be predicated based on statistics derived from $\{T_i(x):i=1-M\}$. For example, T(x) may be determined based on statistics such as the mean or the median of $\{T_i(x):i=1-M\}$, and/or based on statistics derived from $\{T_i(y):i=1-M, y\in\varnothing\}$, where $\varnothing$ is a set of electrode locations that are within a spatial neighborhood centered on x.

FIG. 9 is a flowchart of an example method 900 for generating an electro-anatomical map of the heart, based on which one or more features of the disclosure may be implemented. The method 900 begins, in step 910, by measuring groups of activation signals. The activation signals of each group may be measured by respective electrodes of a mapping catheter that is placed at a respective position in the heart. The mapping catheter may be placed in positions within the heart, so that one or more electrodes that measure activation signals of one group spatially overlap with respective electrodes that measure activation signals of other groups. In an aspect, electrodes are determined to be overlapping, if their distance from each other is below a predetermined threshold. Based on the measured groups of activation signals, in step 920, respective sets of time measurements may be obtained, utilizing the overlapping electrodes, as explained above in reference to FIG. 7 and FIG. 8. Based on the obtained sets of time measurements, the electro-anatomical map may be constructed in step 930. Further aspects of method 900 are described below.

In a first aspect, obtaining a time measurement of a first set (of the time measurement sets) may be based on an activation signal of a respective first group (of the signal activation groups), where the time measurement is computed relative to a time-reference provided by a first activation signal of the first group (e.g., such as time measurement 750.1-$T_B$ that may be computed based on time-reference 750.1-$T_A$ 752 provided by activation signal 750.1-A).

In a second aspect, obtaining a time measurement of a second set (of the time measurement sets) may be based on an activation signal of a respective second group (of the signal activation groups), where the time measurement is computed relative to another time measurement obtained based on an activation signal of another group, and where the activation signal of the other group was measured by a first electrode that overlapped a second electrode that measured an activation signal of the second group (e.g., such as time measurement 750.2-$T_B$ that is computed relative to time measurement 750.1-$T_C$ that was obtained based on an activation signal 750.1-C, where activation signal 750.1-C was measured by electrode 730.1-C that overlapped electrode 730.2-A that measured activation signal 750.2-A). Note that in the second aspect, the time measurement may be adjusted based on a degree of overlap between the first electrode and the second electrode. Furthermore, a certainty metric may be associated with the time measurement based on such degree of overlap.

Hence, certainty metrics may be computed for respective time measurements. In an aspect, certainty metrics may be computed based on the shape of respective activation signals. For example, the certainty metrics of respective time measurements that are associated with electrode locations within a small neighborhood can be determined based on the morphological similarity of unipolar electrical signals measured by those electrodes. Accordingly, the time measurements may be filtered based on their respective certainty metrics when constructing the electro-anatomical map.

Although features and elements are described above in particular combinations, one of ordinary skill in the art will appreciate that each feature or element can be used alone or in any combination with the other features and elements. In addition, although process steps are described above in a particular order, the steps can be performed in other desirable orders.

The methods, processes, modules, and systems described herein may be implemented in a computer program, software, or firmware incorporated in a computer-readable medium for execution by a computer or processor. Examples of computer-readable media include electronic signals (transmitted over wired or wireless connections) and computer-readable storage media. Examples of computer-readable storage media include, but are not limited to, read only memory (ROM), random access memory (RAM), a register, cache memory, semiconductor memory devices, magnetic media such as internal hard disks and removable disks, magneto-optical media, and optical media such as CD-ROM disks, and digital versatile disks (DVDs). A processor in association with software may be used to implement a radio frequency transceiver for use in a WTRU, UE, terminal, base station, RNC, or any host computer.

Further embodiments herein may be formed by supplementing an embodiment with one or more element from any one or more other embodiments herein, and/or substituting one or more elements from one embodiment with one or more elements from one or more other embodiment herein.

It is understood, therefore, that the disclosed subject matter is not limited to the particular embodiments disclosed, but is intended to cover all modifications which are within the spirit and scope of the disclosure as defined by the appended claims, the above description, and/or shown in the attached drawings.

What is claimed is:

1. A method for generating an electro-anatomical map of a heart during a cardiac ablation procedure, the method comprising:

measuring, by respective electrodes of a mapping catheter positioned within the heart during the cardiac ablation procedure, groups of activation signals, the activation signals of each group being measured while the mapping catheter is at a respective position in the heart during a corresponding time interval, wherein at least one electrode that measured an activation signal of a first group spatially overlaps a respective electrode that measured a respective activation signal of a second group and two electrodes are deemed to spatially overlap when a distance between their respective spatial coordinates is less than a predetermined threshold;

deriving, based on a respective spatial overlap between electrodes of different groups, relative timing information between the groups of activation signals;

obtaining, based on the groups of activation signals and the relative timing information, respective sets of time measurements;

constructing, based on the respective sets of time measurements, the electro-anatomical map that associates activation times with corresponding spatial locations of the heart; and displaying, on a display of a console during the cardiac ablation procedure, the electro-anatomical map contemporaneously with the measuring.

2. The method of claim 1, wherein the obtaining further comprises:

computing a time measurement of a first set of the respective sets based on the activation signal of a respective first group, the time measurement being computed relative to a time reference provided by a first activation signal of the first group.

3. The method of claim 2, wherein the obtaining further comprises:

computing a time measurement of a second set of the respective sets based on the activation signal of a respective second group, the time measurement being computed relative to another time measurement obtained based on an activation signal of another group, wherein the activation signal of the other group was measured by a first electrode that overlaps a second electrode that measured the activation signal of the second group.

4. The method of claim 3, wherein the computing of the time measurement of the second set further comprises:

adjusting the time measurement of the second set based on a degree of overlap between the first electrode and the second electrode.

5. The method of claim 3, wherein the obtaining further comprises:

for each respective time measurement of the respective sets of time measurements, computing a certainty metric by the console.

6. The method of claim 5, wherein the certainty metric associated with the time measurement of the second set is computed based on a degree of overlap between the first electrode and the second electrode.

7. The method of claim 5, wherein the certainty metric associated with a time measurement is computed based on a shape of an activation signal measured by the respective electrode.

8. The method of claim 5, wherein the constructing of the electro-anatomical map further comprises:

filtering, based on the certainty metrics, the respective time measurements of the respective sets of time measurements.

9. The method of claim 3, wherein the obtaining further comprises:

computing multiple versions of the respective sets of time measurements, wherein for each version, when computing the time measurement of the second set, the other group is a different group of the groups; and predicting or determining the respective sets of time measurements based on statistics computed from the multiple versions.

10. The method of claim 2, wherein the obtaining further comprises:

computing multiple versions of the respective sets of time measurements, wherein for each version another set of the respective sets is selected as the first set; and predicting or determining the respective sets of time measurements based on statistics computed from the multiple versions.

11. The method of claim 2, wherein the obtaining further comprises:

computing a time measurement of a second set of the respective sets based on the activation signal of a respective second group, the time measurement being computed based on a weighted combination of time elements, wherein each time element is computed relative to a time measurement computed based on an activation signal of another group, wherein the activation signal of the other group was measured by a first electrode that overlaps a second electrode that measured the activation signal of the second group, and a weight associated with each time element is computed based on a degree of overlap between the first electrode and the second electrode.

12. A system for generating an electro-anatomical map of a heart during a cardiac ablation procedure, the system comprising:

a display;

a memory;

a communication interface that is commutatively coupled to at least one catheter; and one or more processors that are commutatively coupled to the communication interface, the memory, and the display;

wherein the one or more processors are collectively configured to:

measure, using the catheter, groups of activation signals, the activation signals of each group being measured by respective electrodes of a mapping catheter placed at respective positions in the heart during corresponding time intervals, wherein at least one electrode that measured an activation signal of a first group spatially overlaps a respective electrode that measured a respective activation signal of a second group and two electrodes are deemed to spatially overlap when a distance between their respective spatial coordinates is less than a predetermined threshold;

derive, based on a spatial overlap between electrodes of different groups, relative timing information between the groups of activation signals;

obtain, based on the groups of activation signals and the relative timing information, respective sets of time measurements;

construct, based on the respective sets of time measurements, the electro-anatomical map that associates activation times with corresponding spatial locations of the heart; and cause the electro-anatomical map to be displayed on the display during the cardiac ablation procedure contemporaneously with the measuring.

13. The system of claim 12, wherein the respective sets of time measurements are obtained by:

computing a time measurement of a first set of the respective sets based on the activation signal of a respective first group, the time measurement being computed relative to a time reference provided by a first activation signal of the first group.

14. The system of claim 13, wherein a time measurement of the first set is computed by:

computing multiple versions of the respective sets of time measurements; and predicting or determining the respective sets of time measurements based on statistics computed from the multiple versions, wherein:

(i) for each version, when computing a time measurement of a second set, the other group is a different group of the groups, or (ii) for each version, another set of the respective sets is selected as the first set.

15. The system of claim 13, wherein the respective sets of time measurements are further obtained by:

computing a time measurement of a second set of the respective sets based on the activation signal of a respective second group, the time measurement being computed based on a weighted combination of time elements, wherein each time element is computed relative to a time measurement computed based on an activation signal of another group, wherein the activation signal of the other group was measured by a first electrode that overlaps a second electrode that measured the activation signal of the second group, and a weight associated with each time element is computed based on a degree of overlap between the first electrode and the second electrode.

16. The system of claim 12, wherein the respective sets of time measurements are obtained by:

computing a time measurement of a second set of the respective sets based on the activation signal of a respective second group, the time measurement being computed relative to another time measurement obtained based on an activation signal of another group, wherein the activation signal of the other group was measured by a first electrode that overlaps a second electrode that measured the activation signal of the second group.

17. The system of claim 16, wherein the computing the time measurement of the second set comprises adjusting the time measurement of the second set based on a degree of overlap between the first electrode and the second electrode.

18. The system of claim 16, wherein obtaining further comprises, for each time measurement of the respective sets of time measurements, computing a certainty metric, and wherein the certainty metric associated with the time measurement of the second set is computed based on a degree of overlap between the first electrode and the second electrode.

19. The system of claim 18, wherein the electro-anatomical map further is constructed by:

filtering, based on the certainty metrics, the respective time measurements of the respective sets of time measurements.

20. A non-transitory computer-readable medium comprising instructions executable by at least one processor of a console to perform a method for generating an electro-anatomical map of a heart during a cardiac ablation procedure, the method comprising:

measuring, by respective electrodes of a mapping catheter positioned within the heart during the cardiac ablation procedure, groups of activation signals, the activation signals of each group being measured while the mapping catheter is at a respective position in the heart during a corresponding time interval, wherein at least one electrode that measured an activation signal of a first group spatially overlaps a respective electrode that measured a respective activation signal of a second group and two electrodes are deemed to spatially overlap when a distance between their respective spatial coordinates is less than a predetermined threshold;

deriving, based on a spatial overlap between electrodes of different groups, relative timing information between the groups of activation signals;

obtaining, based on the groups of activation signals and the relative timing information, respective sets of time measurements;

constructing, based on the respective sets of time measurements, the electro-anatomical map that associates activation times with corresponding spatial locations of the heart; and displaying, on a display of the console during the cardiac ablation procedure, the electro-anatomical map contemporaneously with the measuring.

*    *    *    *    *